US005747255A

United States Patent [19]

Brenner

[11] Patent Number: 5,747,255
[45] Date of Patent: May 5, 1998

[54] POLYNUCLEOTIDE DETECTION BY ISOTHERMAL AMPLIFICATION USING CLEAVABLE OLIGONUCLEOTIDES

[75] Inventor: Sydney Brenner, Cambridge, England

[73] Assignee: Lynx Therapeutics, Inc., Hayward, Calif.

[21] Appl. No.: 536,743

[22] Filed: Sep. 29, 1995

[51] Int. Cl.$^6$ ............... C12Q 1/68; C12P 19/34
[52] U.S. Cl. ............... 435/6; 435/912
[58] Field of Search ............... 435/6, 91.2, 91.21; 935/77, 78

[56] References Cited

U.S. PATENT DOCUMENTS

| | | | |
|---|---|---|---|
| 4,683,195 | 7/1987 | Mullis et al. | 435/91.2 |
| 4,775,619 | 10/1988 | Urdea | 435/6 |
| 4,876,187 | 10/1989 | Duck | 435/6 |
| 5,011,769 | 4/1991 | Duck | 435/6 |
| 5,118,605 | 6/1992 | Urdea | 435/6 |
| 5,367,066 | 11/1994 | Urdea | 536/24.3 |
| 5,380,833 | 1/1995 | Urdea | 536/22.1 |
| 5,409,818 | 4/1995 | Davey | 435/91.21 |
| 5,422,252 | 6/1995 | Walker | 435/91.2 |

FOREIGN PATENT DOCUMENTS

| | | |
|---|---|---|
| 0 477 011 A2 | 3/1992 | European Pat. Off. . |
| WO 89/02984 | 10/1989 | WIPO . |
| WO 93/10264 | 5/1993 | WIPO . |
| WO 95/05480 | 2/1995 | WIPO . |
| WO 95/14106 | 5/1995 | WIPO . |

OTHER PUBLICATIONS

Duck et al, "Probe amplifier system based on chimeric cycling oligonucleotides," BioTechniques, 9: 142148 (1990).

Okano et al, "DNA probe assay based on exonuclease III digestion of probes hybridized on target DNA," Anal. Biochem., 228: 101–108 (1995).

Walker, "Empirical aspects of strand displacement amplification," PCR Methods and Applications, 3: 1–6 (1993).

Walker et al, "Isothermal in vitro amplification of DNA by a restriction enzyme/DNA polymerase system," Proc. Natl. Acad. Sci., 89: 392–396 (1992).

Primary Examiner—Lisa B. Arthur
Attorney, Agent, or Firm—Stephen C. Macevicz; Vincent M. Powers

[57] ABSTRACT

A method for detecting a target polynucleotide is provided which relies on the exponential amplification of oligonucleotide fragments. Separated populations of oligonucleotides are provided that contain complementary sequences to one another and that contain at least one scissile linkage which is cleaved whenever a perfectly matched duplex is formed containing the linkage. When a target polynucleotide contacts a first oligonucleotide cleavage occurs and a first fragment is produced which can hybridize with a second oligonucleotide. Upon such hybridization, the second oligonucleotide is cleaved releasing a second fragment that can, in turn, hybridize with a first oligonucleotide in a manner similar to that of the target polynucleotide. Upon such hybridization, cleavage again occurs and an additional first fragment is produced which can hybridize

10 Claims, 5 Drawing Sheets

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 26 nucleotides
( B ) TYPE: nucleic acid
( C ) STRANDEDNESS: single
( D ) TOPOLOGY: linear ( x i ) SEQUENCE DESCRIPTION: SEQ ID NO: 1:

TTTGACTCTG ATACATCUGA CACGGT                      2 6

( 2 ) INFORMATION FOR SEQ ID NO: 2:

( i ) SEQUENCE CHARACTERISTICS:
( A ) LENGTH: 23 nucleotides
( B ) TYPE: nucleic acid
( C ) STRANDEDNESS: single
( D ) TOPOLOGY: linear ( x i ) SEQUENCE DESCRIPTION: SEQ ID NO: 2:

ACCGTGTCAG ATGTAUCAGA GTC                         2 3

( 2 ) INFORMATION FOR SEQ ID NO: 3:

( i ) SEQUENCE CHARACTERISTICS:
( A ) LENGTH: 45 nucleotides
( B ) TYPE: nucleic acid
( C ) STRANDEDNESS: single
( D ) TOPOLOGY: linear ( x i ) SEQUENCE DESCRIPTION: SEQ ID NO: 3:

TCGACTGCAA GTACCACCGT GTCAGATGTA GTACTCTCGC AGATG   4 5

POLYNUCLEOTIDE DETECTION BY ISOTHERMAL AMPLIFICATION USING CLEAVABLE OLIGONUCLEOTIDES

FIELD OF THE INVENTION

The invention relates generally to a method and compositions for detecting a polynucleotide, and more specifically, to a method and compositions for producing an exponentially growing signal in the presence of a target polynucleotide under isothermal conditions.

BACKGROUND

Many disease states are associated with rearrangements, deletions, or additions of genetic material. Such alterations may be inherited, as in the case of genetic disorders, e.g. sickle cell disease, phenylketonuria, cystic fibrosis, and the like; or they may be acquired, as in the case of some cancers, e.g. chronic myelogenous leukemia, and some infectious diseases, e.g. Epstein-Barr virus infections. As the understanding of the molecular basis for such disease states has increased, diagnostic techniques utilizing DNA probes have been developed which are based on the direct detection of DNA sequences associated with the disease conditions, e.g. Landegren et al, Science, 242: 229–237 (1988); Caskey, Science, 236: 1223–1229 (1987); and Keller et al, DNA Probes, Second Edition (Stockton Press, New York, 1993). These techniques have also found application in a host of other areas ranging from forensic science, e.g. for detecting the presence of polymorphic forms of genes, to veterinary science, e.g. for confirming and/or determining pedigrees, to food science, e.g. for detecting the presence of pathogens, to many other related disciplines.

Generally, application of the above techniques depends on two factors: (1) the ability to acquire a sufficient amount of target DNA for analysis, and (2) the means for generating a signal to indicate the presence or absence of the target DNA, or in some cases to indicate the quantity of target DNA present, e.g. Matthews and Kricka, Anal. Biochem. 169: 1–25 (1988). Specific techniques are often limited for a variety of reasons relating to these factors. For example, restriction fragment length polymorphism (RFLP) analysis requires a relatively large amount of DNA for analysis. In other cases, applicability is limited, or rendered more difficult, because components of a diagnostic sample must be separated for subsequent detection of the target DNA, e.g. by electrophoresis, chromatography, filtering, or the like. And in still other cases, the amount of starting target material may be so small, or the amount of interfering material in a sample may be so great, that detection or quantitation is beyond a technique's level of sensitivity.

Many of these problems have been addressed by recently developed nucleic acid detection and amplification techniques, e.g. polymerase chain reaction (PCR), Mullis, U.S. Pat. No. 4,683,202; ligase-based techniques, e.g. reviewed by Barany, PCR Methods and Applications 1: 5–16 (1991); strand-displacement amplification, Walker et al, U.S. Pat. No. 5,422,252; reverse transcriptase-based techniques, e.g. Davey et al, U.S. Pat. No. 5,409,818; Qβ replicase-based techniques, e.g. Chu et al, U.S. Pat. No. 4,957,858; branched DNA techniques, Urdea et al, U.S. Pat. No. 5,124,246; techniques employing RNA-DNA chimeric probes, Duck et al, U.S. Pat. No. 5,011,769; and the like.

In many cases, these techniques have lead to commercially significant diagnostic and forensic assays. But in many other cases, problems still remain, such as spurious amplification of contaminating sequences which lead to false-positive read-outs. e.g. Arnheim and Erlich, Annu. Rev. Biochem., 61: 131–156 (1992); and McPherson et al, editors, PCR: A Practical Approach (IRL Press, Oxford, 1991); difficult-to-synthesize assay components; and the high cost of gaining access to proprietary assay methods or components, which can vitiate the commercial incentive to develop products.

In view of the above, the availability of a simple and sensitive alternative method for rapidly generating a signal to indicate the presence or absence of a target DNA without the need of post-amplification handling would facilitate the scientific and commercial application of DNA-based assays, especially in clinical and forensic settings.

SUMMARY OF THE INVENTION

An object of my invention is to provide a method of detecting a target polynucleotide that is rapid and highly sensitive.

Another object of my invention is to provide compositions for exponential amplification of a signal indicating the presence of a target polynucleotide.

Another object of my invention is to provide an assay for the presence of a single-stranded target polynucleotide that requires only minimal post-amplification manipulation for a read-out.

These and other objects are accomplished by providing a method and materials for exponentially amplifying nucleic acid fragments when placed in contact with a target polynucleotide. In accordance with the method of the invention, first and second oligonucleotides having complementary sequences to one another are provided that are separated so that the formation of duplexes between them is substantially or totally inhibited. Each first and second oligonucleotide contains at least one scissile linkage which is cleaved whenever a perfectly matched duplex is formed containing the linkage. Upon exposure to a target polynucleotide, an initial duplex forms between the target polynucleotide and a first oligonucleotide which contains the scissile linkage. The first oligonucleotide is cleaved at the scissile linkage releasing a first fragment, the first fragment containing the complementary sequence to the second oligonucleotide. The released first fragment is then free to diffuse to and hybridize with the complementary portion of a second oligonucleotide to form a perfectly matched duplex containing the second oligonucleotide's scissile linkage. Upon formation of the duplex, the linkage is cleaved releasing a second fragment which contains the complementary sequence to the first oligonucleotides. The released second fragment is then free to diffuse to and hybridize with the complementary portion of a first oligonucleotide to form a perfectly matched duplex containing the scissile linkage. The linkage is cleaved releasing yet another first fragment which is free to diffuse to and hybridize with the complementary portion of a second oligonucleotide. Thus, a chain of cleavage reactions is initiated by the initial exposure to a target polynucleotide.

As explained more fully below, a variety of scissile linkages may be employed with the invention. Preferably, a scissile linkage is created by providing first and second oligonucleotides comprised of deoxyribonucleotide and ribonucleotide monomers, such that cleavage occurs at a ribonucleotide moiety upon the formation of a duplex in the presence of RNase H, or enzyme of like activity.

Preferably, the first and second oligonucleotides are substantially physically separated (or equivalently stated, maintained in substantial physical separation) by anchoring them either to separate solid phase supports or to separate regions of the same solid phase support.

3

The invention includes compositions and kits for implementing the preferred embodiments. Generally, kits of the invention include first and second oligonucleotides attached to their respective solid phase supports, buffers, and other reagents for carrying out the cleavage reactions.

Definitions

The term "oligonucleotide" as used herein includes linear oligomers of natural or modified monomers or linkages, including deoxyribonucleosides, ribonucleosides, α-anomeric forms thereof, peptide nucleic acids (PNAs), polynucleotide analogs having phosphoramidate internucleoside linkages, and the like, that are capable of specifically binding to a target polynucleotide by way of a regular pattern of monomer-to-monomer interactions, such as Watson-Crick type of base pairing, base stacking, or the like. Usually, monomers are linked by phosphodiester bonds or analogs thereof to form oligonucleotides ranging in size from a few monomeric units, e.g. 3-4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce degeneracy, increase specificity, and the like. "Perfectly matched duplex" in reference to primers and target polynucleotides means that a primer forms a double stranded structure with a complementary sequence of nucleotides on the target polynucleotide so that each nucleotide in the double stranded structure undergoes Watson-Crick base pairing with a nucleotide on the opposite strand.

DETAILED DESCRIPTION OF THE INVENTION

Figure 1A:
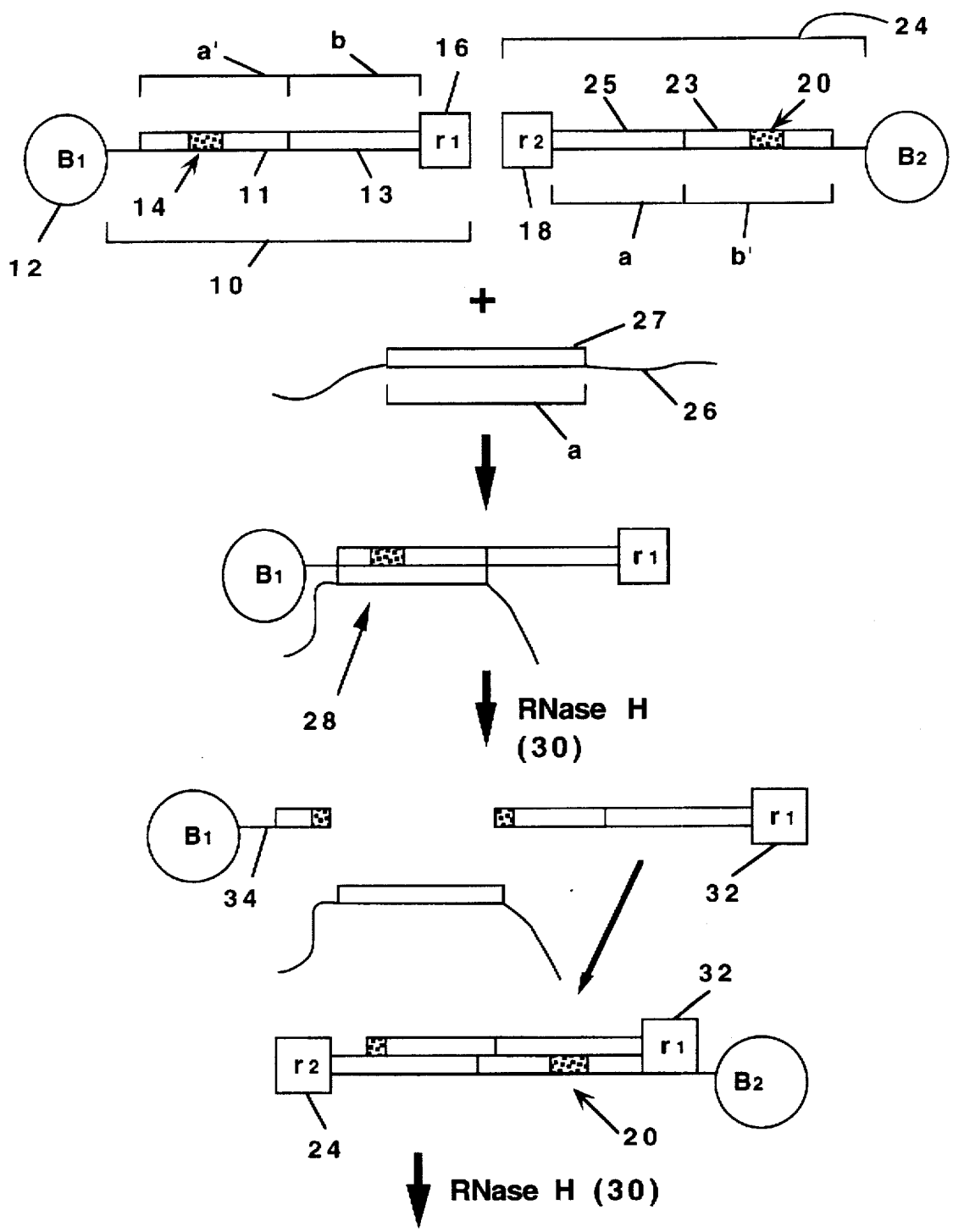
FIGS. 1a and 1b diagrammatically illustrate the first few steps of the chain of cleavage reactions initiated in response to the presence of a target polynucleotide in a preferred embodiment employing RNase H.

In the method of the invention a target polynucleotide triggers a chain of cleavage reactions that cause the exponential amplification of oligonucleotide fragments. The amplification of the fragments provides a direct or indirect signal indicating the presence of the target polynucleotide.

Preferably, the method of the invention comprises the following steps: a) A first oligonucleotide is provided having a nucleotide sequence complementary to a portion of the target polynucleotide and a scissile linkage which is cleaved whenever the first oligonucleotide forms a perfectly matched duplex with the target polynucleotide. Preferably, this duplex contains the scissile linkage. Upon cleavage, a first fragment is released from the first oligonucleotide leaving a truncated first oligonucleotide. The first fragment contains a nucleotide sequence identical to that of a portion of the target polynucleotide. b) A second oligonucleotide is provided having a nucleotide sequence identical to that of a portion of the first fragment and a scissile linkage which is cleaved whenever the second oligonucleotide forms a perfectly matched duplex with the first fragment. Again, this duplex preferably contains the scissile linkage of the second oligonucleotide. The portions of the target polynucleotide and first fragment are large enough to permit hybridization under the selected reaction conditions. Typically, the portions are in the range of 12 to 30 nucleotides in length.

Upon cleavage, a second fragment is released from the second oligonucleotide leaving a truncated second oligonucleotide. The second fragment contains a nucleotide sequence identical to that of a portion of the first oligonucleotide. c) The first and second oligonucleotides are maintained in substantial physical separation such that the formation of perfectly matched duplexes between them is substantially inhibited and such that released first and second fragments may diffusibly communicate with the second and first oligonucleotides, respectively. d) The first oligonucleotide is exposed to the target polynucleotide under conditions i) where stable duplexes can form between the following: the first oligonucleotide and the complementary portion of the target polynucleotide, the first oligonucleotide and the second fragment, and the second oligonucleotide and the first fragment, and ii) where stable duplexes fail to form between truncated first oligonucleotides and second fragments and between truncated second oligonucleotides and first fragments. Under such conditions the concentrations of the first and second fragments increase exponentially in indication of the presence of the target polynucleotide.

Generally, the selection of reaction conditions depends on several factors, including the length and composition of the portions of the first and second oligonucleotides that form duplexes, the position of the scissile linkages within the duplexes, limitations on the composition of the first and second oligonucleotides imposed by the target polynucleotide, salt concentration, temperature, constraints imposed by the use of ancillary enzymes, such as RNase H, and the like. Extensive guidance for making such selections or design choices can be found in numerous references, including Wetmur, Critical Reviews in Biochemistry and Molecular Biology, 26: 227–259 (1991); Hames and Higgins, editors, Nucleic Acid Hybridization: A Practical Approach (IRL Press, Oxford, 1985); Breslauer et al, Proc. Natl. Acad. Sci., 83: 3746–3750 (1986); McGraw et al, Biotechniques, 8: 674–678 (1990); Walker, PCR Methods and Applications, 3: 1–6 (1993); and the like.

Preferably, the stringency of reaction conditions in the method is controlled by selecting a reaction temperature that i) permits stable duplexes to form between the first oligonucleotide and the complementary portion of the target polynucleotide, the first oligonucleotide and the second fragment, and the second oligonucleotide and the first fragment and ii) inhibits the formation of stable duplexes between truncated first oligonucleotides and second fragments and between truncated second oligonucleotides and first fragments. That is, the method of the invention is preferably carried out under isothermal conditions at a temperature i) substantially below the melting temperature of the duplexes formed between the first oligonucleotide and the complementary portion of the target polynucleotide, the first oligonucleotide and the second fragment, and the second oligonucleotide and the first fragment and ii) substantially above the melting temperature of the duplexes formed between truncated first oligonucleotides and second fragments and between truncated second oligonucleotides and first fragments. Preferably, the reaction temperature is i) at least 5° C. below the lowest melting temperature of the duplexes formed between the first oligonucleotide and the complementary portion of the target polynucleotide, the first oligonucleotide and the second fragment, and the second oligonucleotide and the first fragment and ii) at least 5° C. above the melting temperature of the duplexes formed between truncated first oligonucleotides and second fragments and between truncated second oligonucleotides and first fragments. Under these, or equivalent conditions, the following duplexes tend to dissociate: those formed between truncated first oligonucleotides and second fragments and between truncated second oligonucleotides and first fragments. Likewise, under these, or equivalent conditions, the following duplexes tend to remain intact: those formed between the first oligonucleotide and the complementary portion of the target polynucleotide, the first oligonucleotide and the second fragment, and the second oligonucleotide and the first fragment. Such conditions are readily implemented with any number of commercially available heating blocks or thermal cycling instruments. In preferred embodiments of the invention, typical duplex lengths will lie in the range of 5 to 30 nucleotides. Typically, reactions of the invention are carried out in microfuge tubes, microtiter plate wells, or like vessels, and reaction volumes are typically in the range of 1 to 250 μL. Reaction temperature depends on several factors, including the constraints imposed on particular embodiments by the operating range and salts requirements of the ancillary enzymes employed, the presence or absence of organic solvents, such as dimethyl sulfoxide, glycerol, 1-methyl-2-pyrrolidinone, or the like, the selection of target polynucleotide sequences for detection, the position of the scissile linkage, and the like. Guidance for making design choices based on these factors is found in the above references, particularly Wetmur (cited above) and Breslauer et al (cited above). Typically, the reaction temperature falls within the range of about 32° C. to about 60° C. More preferably, the reaction temperature falls within the range of about 35° C. to about 50° C.

First and second oligonucleotides of the invention are usually synthesized with conventional techniques, e.g. a Perkin-Elmer (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. However, as explained more fully below, some scissile linkages may require the use of special monomers, e.g. abasic monomers, or the like, such as disclosed in Urdea and Horn, U.S. Pat. No. 5,367,066, or the use of nuclease-resistant internucleoside linkages, such as, phosphorothioates, methylphosphonates, phosphoramidates, or other phosphate analogs, such as widely disclosed in the antisense therapeutics literature, e.g. Uhlmann et al, Chemical Reviews, 90: 543–584 (1990). Embodiments requiring oligonucleotides with RNA segments may be synthesized with conventional protocols, e.g. via phosphoramidite chemistry, using commercially available reagents, e.g. Perkin-Elmer (Foster City, Calif.).

An important feature of the invention is the substantial separation of the first and second oligonucleotides to minimize self-initiation of the chain of cleavage reactions. Such separation can be achieved by a variety of methods such as compartmentalization with filtration or dialysis membranes, liposomes, or the like. Preferably, such separation is accomplished by anchoring the first and second oligonucleotides either to separate solid phase supports or to separate regions of the same solid phase support. The separated first and second oligonucleotides must be close enough to permit released first and second fragments diffuse to their respective complements so that a signal can be generated within the range of several tens of minutes to a few, e.g. 2 to 3, hours. Several factors may affect the speed of the assay, including the magnitude of the separation between the first and second oligonucleotides, the nature of the scissile linkage and the mechanism for its cleavage, the size of the released first and second fragments, the presence of viscosity-affecting agents, e.g. agents such as liquid polymers, or gels, to inhibit contact of first and second oligonucleotides, or agents to inhibit nonspecific hybridization of reaction components, e.g. Denhardt's solution, or the like. As used herein, the term "diffusibly communicate" in reference to two or more locations means that a substance at one location may diffuse to the second location where it may participate in a chemical or physical interaction. As discussed more fully below, first and second oligonucleotides are substantially separated by synthesizing them on, or attaching them to, separate microparticles. Such microparticles may then be placed in physical proximity, e.g. by placement in a common reaction vessel, distribution on a wetted surface such as a microscope slide, microtiter plate well, membrane, or the like.

Solid phase supports for use with the invention may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. First and second oligonucleotides may be used with the solid phase support that they are synthesized on, or they may be separately synthesized and attached to a solid phase support for use, e.g. as disclosed by Lund et al, Nucleic Acids Research, 16: 10861–10880 (1988); Albretsen et al, Anal. Biochem., 189: 40–50 (1990); Wolf et al, Nucleic Acids Research, 15: 2911–2926 (1987); or Ghosh et al, Nucleic Acids Research, 15: 5353–5372 (1987). Preferably, first and second oligonucleotides are synthesized on and used with the same solid phase support, which may comprise a variety of forms and include a variety of linking moieties. Such supports may comprise microparticles or arrays, or matrices, of regions where uniform populations of first or second oligonucleotides are synthesized. A wide variety of microparticle supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678,814; 4,413,070; and 4,046,720; and Pon, Chapter 19, in Agrawal, editor, Methods in Molecular Biology, Vol. 20, (Humana Press, Totowa, N.J., 1993). Microparticle supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on particular embodiments. For example, in applications involving successive processing with enzymes, supports and linkers that minimize steric hinderance of the enzymes and that facilitate access to substrate are preferred. Exemplary linking moieties are disclosed in Pon et al, Biotechniques, 6:768–775 (1988); Webb, U.S. Pat. No. 4,659,774; Barany et al, International patent application PCT/US91/06103; Brown et al, J. Chem. Soc. Commun., 1989: 891–893; Damha et al, Nucleic Acids Research, 18: 3813–3821 (1990); Beattie et al, Clinical Chemistry, 39: 719–722 (1993); Maskos and Southern, Nucleic Acids Research, 20: 1679–1684 (1992); and the like.

As mentioned above, first and second oligonucleotides may be synthesized on a single (or a few) solid phase support to form an array of regions uniformly coated with first and second oligonucleotides. Techniques for synthesizing such arrays are disclosed in McGall et al, International application PCT/US93/03767; Pease et al, Proc. Natl. Acad. Sci., 91: 5022–5026 (1994); Southern and Maskos, International application PCT/GB89/01114; Maskos and Southern (cited above); Southern et al, Genomics, 13: 1008–1017 (1992); and Maskos and Southern, Nucleic Acids Research, 21: 4663–4669 (1993).

Preferably, the invention is implemented with microparticles or beads uniformly coated with first and second oligonucleotides. Microparticle supports and methods of covalently or noncovalently linking oligonucleotides to their surfaces are well known, as exemplified by the following references: Beaucage and Iyer (cited above); Gait, editor, Oligonucleotide Synthesis: A Practical Approach (IRL Press, Oxford, 1984); and the references cited above. Generally, the size and shape of a microparticle is not critical; however, microparticles in the size range of a few, e.g. 1–2, to several hundred, e.g. 200–1000 μm diameter are preferable. Magnetic microparticles are particularly useful as solid phase synthesis supports, such as disclosed by Albretsen et al, Anal. Biochem. 189: 40–50 (1990), as they permit easy separation of the microparticles from the fragments cleaved from the first and second oligonucleotide.

Scissile linkages for use in the invention may be implemented in a variety of ways. Important functional characteristics of such linkages include chemical stability when the first or second oligonucleotide is in single stranded form and chemical lability whenever the first or second oligonucleotide is in double stranded form, preferably as a perfectly matched duplex with another strand of DNA. The exponential amplification of the invention does not depend on the chemical or enzymatic details of the scissile linkage. Usually, a moiety in the first or second oligonucleotide, such as a phosphate linkage, is rendered scissile by the presence of an additional reagent, such as an enzyme whose typical substrate is a DNA-DNA or RNA-DNA duplex. In some embodiments, special monomers may be inserted into the first and/or second oligonucleotides to create a scissile linkage, e.g. an abasic monomer can be employed with enzymes with AP endonuclease activity, such as $E.$ $coli$ exonuclease III, to create a scissile linkage.

Figure 1B:
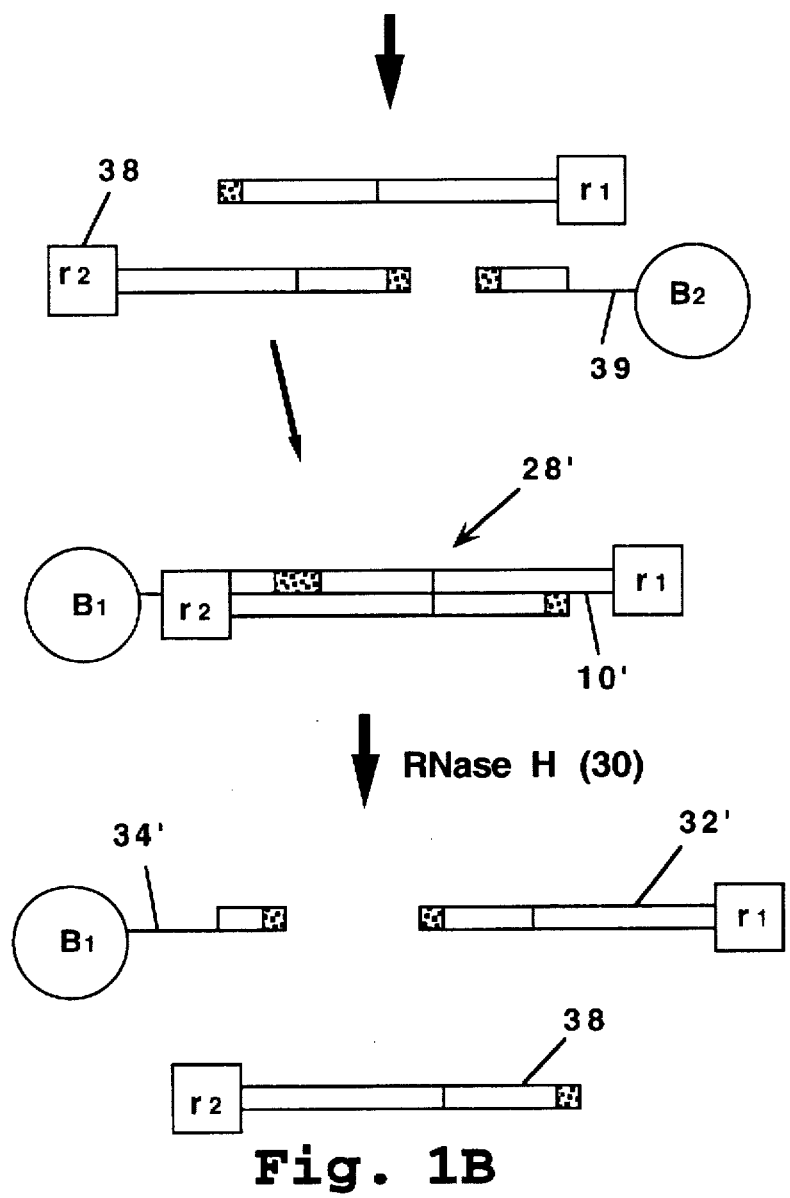

In one preferred embodiment, shown diagrammatically in FIGS. 1a and 1b, the first and second oligonucleotides contain RNA segments that form a scissile linkage in the presence of RNase H. The first and second oligonucleotides may contain one or more RNA segments, but preferably they contain one RNA segment each. Preferably, these RNA segments are centrally located in the oligonucleotides so that upon cleavage the greatest difference in melting temperatures can be achieved between the fragments and the intact oligonucleotides. Preferably, the RNA segments are from 2 to 10 RNA monomers in length; more preferably, the RNA segments are from 4 to 6 RNA monomers in length. Returning to FIG. 1a, first oligonucleotide (10) is attached to solid phase support (12) labeled "$B_1$", which preferably is a microparticle, such as a magnetic bead. First oligonucleotide (10) comprises (i) region (11) having sequence a' which is complementary to a portion "a" of the target polynucleotide, region (11) containing scissile linkage (14) which comprises a segment of ribonucleotide monomers, (ii) region (13) having sequence b which is complementary to a portion of second oligonucleotide (24), and (iii) reporter (16), labeled "$r_1$". In the same reaction vessel, second oligonucleotide (24) is attached to solid phase support (22) labeled "$B_2$", which likewise preferably is a microparticle, such as a magnetic bead. Second oligonucleotide (24) comprises (i) region (23) having sequence b' which is complementary to sequence b of region (13) of first oligonucleotide (10), region (23) containing scissile linkage (20) which comprises a segment of ribonucleotide monomers, (ii) region (25) having sequence "a" complementary to sequence a' of region (11) of first oligonucleotide (10), and (iii) reporter (18), labeled "$r_2$". Upon addition of target polynucleotide (26) containing portion 27 having sequence "a" complementary to sequence a' of region (11) of first oligonucleotide (10), duplex (28) forms between target polynucleotide (26) and region (11) of first oligonucleotide (10). In the presence of RNase H (30), or like enzyme, first oligonucleotide (10) is cleaved forming first fragment (32) and truncated first oligonucleotide (34). The stringency of the reaction conditions are selected so that the duplexes between truncated first oligonucleotide (34) and target polynucleotide (26) and first fragment (32) and target polynucleotide (26) are unstable. In other word, the formation of duplexes are not thermodynamically favored. As discussed above, when temperature is employed to control stringency, preferably a reaction temperature is selected which is above the melting temperatures of the target polynucleotide-first fragment duplex and the target polynucleotide-truncated first oligonucleotide duplex, but below the melting temperature of the target polynucleotide-first oligonucleotide duplex. In this way, first fragment (32) is automatically released into solution upon cleavage at scissile linkage (14). First fragment (32) can then diffuse to and hybridize with second oligonucleotide (24) to form duplex (36). Upon cleavage of scissile linkage (20) by RNase H (30), second fragment (38) and truncated second oligonucleotide (39) are formed. As with first fragment (32), second fragment (38) is released into solution because the stringency of the reaction is selected to ensure that the duplex between second fragment (38) and first fragment (32) is unstable. Released second fragment (38) can then diffuse to and hybridize with first oligonucleotide (10') to form duplex (28'), which leads to the cleavage of first oligonucleotide (10') and the formation of first fragment (32') and truncated first oligonucleotide (34'). First fragment (32'), along with the previously produced first fragment (32), is then free to diffuse to and hybridize with another second oligonucleotide to initiate additional cleavage reactions. Thus, during the initial stages of the chain of cleavage reactions, the number of first and second fragments doubles its current value per each unit of time elapsed.

In this embodiment, the presence of non-sequence-specific RNase activity can be readily monitored by providing a third oligonucleotide having an RNA segment and a distinguishable reporter. Preferably, the RNA segment is the same size as those in the first and second oligonucleotides, but is not complementary to any part of the DNA segments of the first or second oligonucleotide. Thus, no template-driven RNase H cleavage will occur. Any cleavage would be due solely to RNase activity. With the presence of a distinguishable reporter, the degree to which non-specific RNase activity contributes to the amplification signal can be assessed.

Figure 2A:
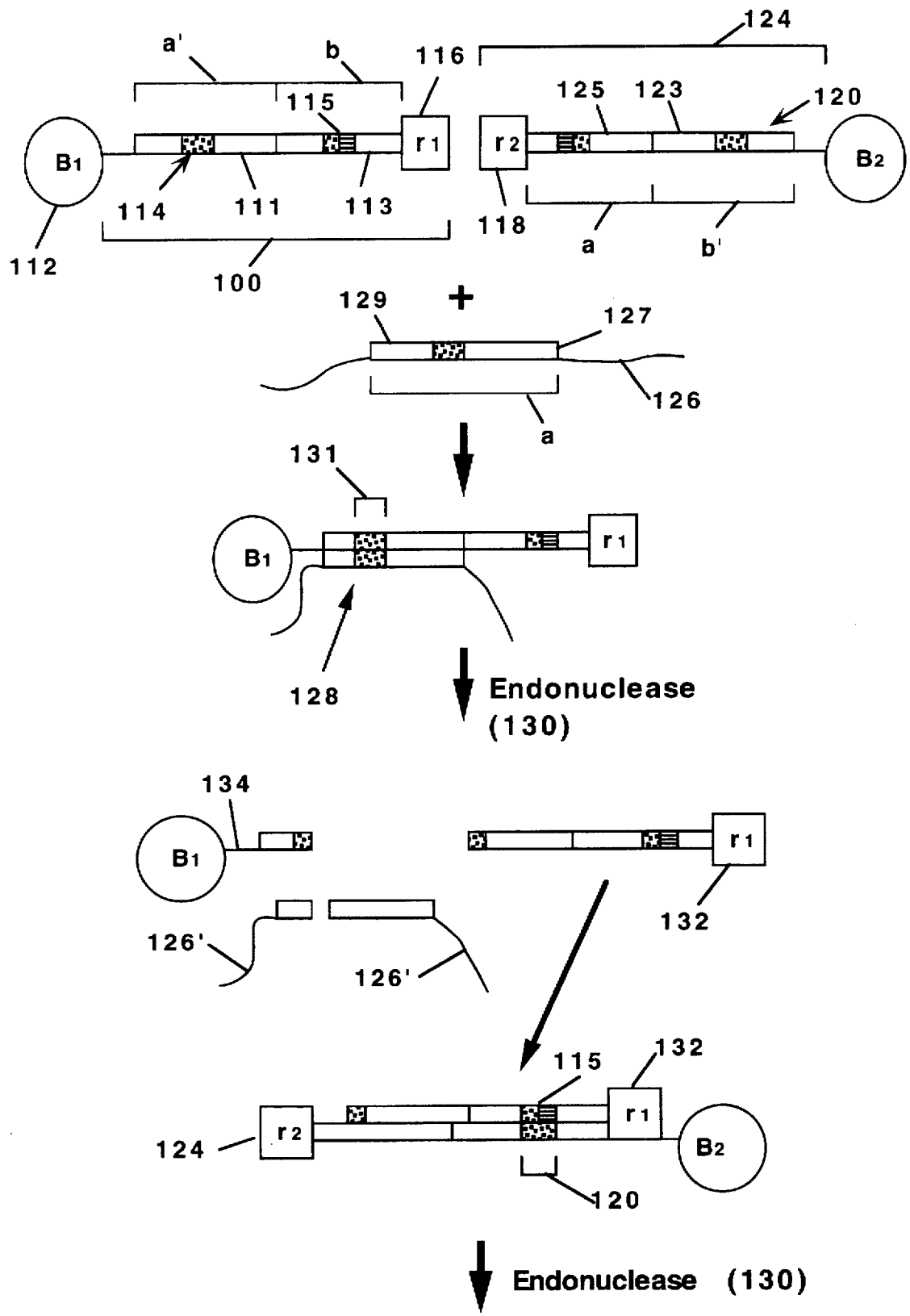
FIGS. 2a and 2b diagrammatically illustrate the first few steps of the chain of cleavage reactions initiated in response to the presence of a target polynucleotide for a preferred embodiment employing a restriction endonuclease.
Figure 2B:
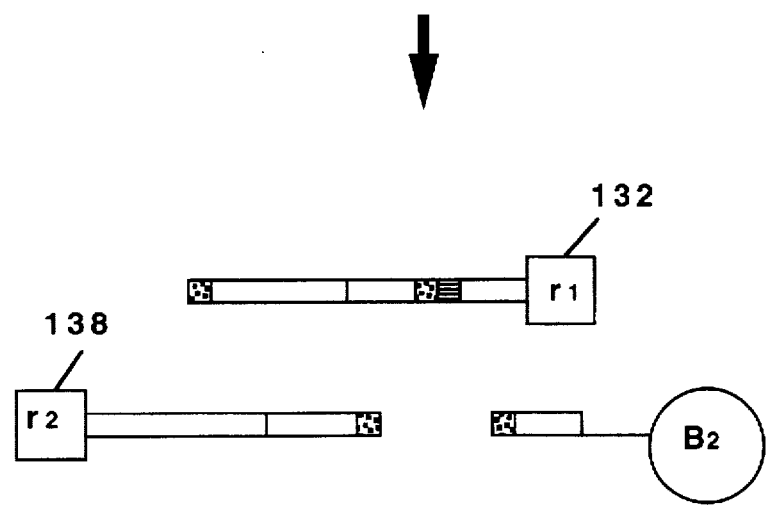

In another preferred embodiment, shown diagrammatically in FIGS. 2a and 2b, strand cleavage is carried out by a restriction endonuclease. In this embodiment, double stranded cleavage is prevented by inserting a nuclease resistant linkage in the portions of the first and second fragments that form the restriction endonuclease cleavage sites with their respective complements. Otherwise, as FIGS. 2a and 2b indicate, the amplification of first and second fragments is similar to that of the embodiment of FIGS. 1a and 1b. First oligonucleotide (100) is attached to solid phase support (112) labeled "$B_1$", which preferably is a microparticle, such as a magnetic bead. First oligonucleotide (100) comprises (i) region (111) having sequence a' which is complementary to a portion "a" of the target polynucleotide, region (111) containing scissile linkage (114) which comprises one strand (114) of a restriction endonuclease recognition site, (ii) region (113) having sequence b which is complementary to a portion of second oligonucleotide (124) and endonuclease-resistant linkage (115), and (iii) reporter (116), labeled "$r_1$". In the same reaction vessel, second oligonucleotide (124) is attached to solid phase support (122) labeled "$B_2$", which likewise preferably is a microparticle, such as a magnetic bead. Second oligonucleotide (124) comprises (i) region (123) having sequence b' which is complementary to sequence b of region (113) of first oligonucleotide (100), region (123) containing scissile linkage (120) which comprises one strand of a restriction endonuclease recognition site, (ii) region (125) having sequence "a" complementary to sequence a' of region (111) of first oligonucleotide (100) and endonuclease-resistant linkage (117), and (iii) reporter (118), labeled "$r_2$". Target polynucleotide (126) contains portion 127 having sequence "a" complementary to sequence a' of region (111) of first oligonucleotide (100) and a complement (129) of the one strand (114) of a restriction endonuclease recognition site. Upon contact of target polynucleotide (126) and first oligonucleotide (100), duplex (128) forms with region (111) of first oligonucleotide (100), the duplex containing restriction endonuclease recognition site (131). In the presence of a restriction endonuclease (130) recognizing site (131), first oligonucleotide (100) is cleaved forming first fragment (132) and truncated first oligonucleotide (134). Endonuclease-resistant linkage (115) prevents first fragment (132) from being cleaved. As above, the stringency of the reaction conditions are selected so that the duplexes between truncated first oligonucleotide (134) and target polynucleotide (126) and first fragment (132) and target polynucleotide (126) are unstable. After cleavage, first fragment (132) can then diffuse to and hybridize with second oligonucleotide (124) to form duplex (136). Upon cleavage of scissile linkage (120) by an endonuclease (130), second fragment (138) and truncated second oligonucleotide (139) are formed. As with first fragment (132), second fragment (138) is released into solution because the stringency of the reaction is selected to ensure that the duplex between second fragment (138) and first fragment (132) is unstable. Released second fragment (138) can then diffuse to and hybridize with first oligonucleotide (100') to form duplex (128'), which leads to the cleavage of first oligonucleotide (100') and the formation of first fragment (132') and truncated first oligonucleotide (134'). First fragment (132'), along with the previously produced first fragment (132), is then free to diffuse to and hybridize with another second oligonucleotide to initiate additional cleavage reactions. Many endonuclease-resistant linkages may be used, and extensive guidance in their selection may be found in the antisense therapeutics literature, e.g. Uhlman et al (cited above). Preferably, a phosphorothioate linkage is employed to confer endonuclease resistance. Such linkages may be synthesized by conventional techniques, e.g. Beaucage et al, U.S. Pat. No. 5,003,097; Stec et al, U.S. Pat. No. 5,151,510; Hirschbein, U.S. Pat. No. 5,166,387; and the like. Guidance for selecting a restriction endonuclease can be found in the strand displacement amplification literature, e.g. Walker et al, U.S. Pat. No. 5,422,252; and Walker, PCR Methods and Applications, 3: 1–6 (1993). Preferred restriction endonucleases include $Taq_I$, $Bst Y_I$.

How a sample containing a target polynucleotide is prepared for use with the invention depends importantly on the source of the sample, which can vary widely, e.g. the source may be blood, homogenized tissue, fixed tissue, tumor biopsies, stool, clinical swabs, food products, hair, plant tissues, microbial culture, public water supply, amniotic fluid, urine, or the like. Moreover, a target polynucleotide may be cloned, synthetic, or natural DNA or RNA; it may be genomic DNA or RNA; or it may be of diverse origin, including mammalian, bacterial, fungal, viral, or plant origin. Whether extraction, purification, or isolation steps are required depends on several factors, including the abundance of the target polynucleotide in the sample, the nature of the target polynucleotide, e.g. whether it is RNA or DNA, the presence of extraneous or associated material such as cell walls, histones, or the like, the presence of enzyme inhibitors, and so on. Extensive guidance is available for selecting the appropriate protocol for particular applications, e.g. Innis et al, Editors, PCR Protocols (Academic Press, San Diego, 1990); Sambrook et al, Molecular Cloning, Second Edition (Cold Spring Harbor Laboratory Press, 1989); Methods in Enzymology, Volumes 6 and 12, parts A and B (Academic Press, New York); McPherson et al, Editors, PCR: A Practical Approach (IRL Press, Oxford, 1991); Herrington et al, Editors, Diagnostic Molecular Pathology: A Practical Approach, Vol. 1 & 2 (IRL Press, Oxford, 1992); and the like. Typically, preparation protocols involve the application of chaotropic agents, e.g. low molecular weight ionic compounds, that favor the solubization of hydrophobic substances, chelating agents, e.g. EDTA, to disable nucleases, proteases to disable nucleases, detergents, pH buffers, and the like, that serve to isolate and/or protect nucleic acids. Optionally, samples may be treated to reduce the size of the target polynucleotide, e.g. by sonication, nuclease treatment, or the like. After such initial preparation steps, preferably a sample is treated to denature, i.e. render single-stranded, the target polynucleotide prior to exposing it to the first oligonucleotide in accordance with the invention. Preferably, denaturation is achieved by heating the sample at 93°–95° C. for five minutes.

Assays employing the method of the invention produce a signal related to the concentration of released first and/or second fragments generated in the chain of cleavage reactions. Preferably, a signal is produced by a reporter or label attached directly or indirectly to the released first and/or second fragments, so that the magnitude of the generated signal increases exponentially with the concentration of the fragments. The first and second fragments of the invention can be labeled in a variety of ways, including the direct or indirect attachment of radioactive moieties, fluorescent moieties, colorimetric moieties, and the like. Many convenient synthetic methodologies are available for producing functionalized oligonucleotides for the attachment of such moieties, including 5' and 3' functionalized oligonucleotides, base-functionalized oligonucleotides, and oligonucleotides functionalized at internucleoside linkages, e.g. Eckstein, Editor, Oligonucleotide Analogues: A Practical Approach (IRL Press, Oxford, 1991); Clontech Laboratories catalog (Clontech Laboratories, Palo Alto, 1993/1994); Hobbs, Jr. U.S. Pat. No. 4,997,928, Fung et al, U.S. Pat. No. 4,757,141, Smith et al, U.S. Pat. No. 4,849,513 (5' functionalities); Reed et al, International patent application PCT/US91/06143, Nelson, U.S. Pat. No. 5,401,837 (3' functionalities); Ruth, U.S. Pat. No. 4,948,882, Urdea et al, U.S. Pat. No. 5,093,232, Hobbs, Jr., U.S. Pat. No. 5,151,507 (base, functionalities); and Agrawal and Zamecnik, Nucleic Acids Research, 18: 5419–5423 (1990), Fidanza et al, J. Am. Chem. Soc., 111: 9117–9119 (1989) (phosphate functionalities). A signal may also be generated by the affect that ligand-bearing first or second fragments have on an evanescent wave in a biosensor when the ligands interact with receptors. Suitable receptors and ligands for such a system are avidin and biotin. A signal may also be generated by the change in frequency characteristics of a piezoelectric crystal due to a mass change caused by the binding of first and/or second fragments to the surface of the crystal.

In one preferred embodiment, first and second oligonucleotides are attached to microparticles, and first and second fragments are labeled directly with a fluorescent dye, such as fluorescein or rhodamine. As the chain of cleavage reactions progress, the concentration of labeled first and second fragments in free solution increases. When the reaction is complete, or after a predetermined time, the microparticles are separated from the reaction solution, after which the fluorescence of the solution is measured. Preferably, the microparticles are magnetic beads for ease of separation. A large number of fluorescent dyes are available for use in this and like embodiments, e.g. Haugland, Handbook of Fluorescent Probes and Research Chemicals (Molecular Probes, Inc., Eugene, 1992) Menchen et al, U.S. Pat. No. 5,188,934; Bergot et al PCT application PCT/US90/05565; and the like.

Preferably, kits for practicing the method of the invention include first oligonucleotides and second oligonucleotides attached to separate solid phase supports, the first and second oligonucleotides being present in sufficient quantity to produce a detectable signal when a chain reaction of cleavages is initiated; and enzyme and reaction buffer for carrying out the cleavage reactions upon contact with a sample. Kits of the invention may also include instructions for particular applications, sample preparation components, and other components related to the detection of the concentration of first and second fragments.

EXAMPLE

Fragment Amplification With Chimeric RNA-DNA Oligonucleotides and RNase H Cleavage In this example, a labeled 26-mer first oligonucleotide and a labeled 23-mer second oligonucleotide were separately synthesized on microparticles, reacted with a test target polynucleotide, and the resultant first and second fragments were analyze by gel electrophoresis. Specifically, the following first (1) and second (2) oligonucleotides (SEQ ID NOS: 1 and 2, respectively) were synthesized on 5 μm GMA beads with non-cleavable linkers (Bangs Laboratories, Carmel, Ind.) using a 4-Primer Assembler DNA sequencer (Pharmacia, Upsala) with the manufacturer's monomers and conventional protocols:

FAM- (5')TTTGACTCTGATACATCugacACGGT(3') - Support    (1)

**************

TET- (5')ACCGTGTCAGATGTaucaGAGTC(3') - Support    (2)

************** where FAM and TET are phosphoramidite-derivatized fluorescein dyes available from Perkin-Elmer, Applied Biosystems Division (Foster City, Calif.). The lower case letters indicate RNA segments; the underlined bases of the first oligonucleotide indicate the complementary portion to the target polynucleotide and the first oligonucleotide; and the underlined bases of the second oligonucleotide indicate the complementary portion between the second fragment and the first oligonucleotide. The asterisks indicate the complementary portions between the second fragment and the first oligonucleotide.

The following target sequence (SEQ ID NO: 3) was prepared on a Perkin-Elmer, Applied Biosystems Division model 394 DNA synthesizer using standard phosphoramidite chemistry:

(5') TCGACTGCAAGTACC
ACCGTGTCAGATGTAGTACTCTCGCAGATG (3')

where the underlined bases indicate the complementary portion between the target polynucleotide and the first oligonucleotide. After cleavage from the synthesis support, the target polynucleotide was purified by reverse phase HPLC, detritylated, and ethanol precipitated using standard protocols.

After synthesis, the first and second oligonucleotides were deprotected as follows: The GMA beads were first treated with NH$_4$OH/ethanol (3:1) (1 mL) at room temperature for 20 hours, after which the solution was decanted and the beads were washed successively with H$_2$O three times, with ethanol three times, and then dried under vacuum for 2 hours. The beads were then treated with 1M tetrabutylammonium fluoride in tetrahydrofuran (THF) at room temperature for another 20 hours. The beads were then washed with THF (3 times), H$_2$O, and ethanol (3 times), after which they were treated with 1M NaCl in H$_2$O (twice) and washed with H$_2$O, ethanol, and then dried under vacuum overnight. Beads were resuspended for use in 40 mM Tris-HCl buffer (pH 7.6). It was estimated that 1 μL of the beads in this suspension contained 2.3 pmol of oligonucleotide.

Four experiments were carried out with the following components:

| Experiment | Reaction Components |
| --- | --- |
| 1 | First oligonucleotide, second oligonucleotide, target polynucleotide, RNase H |
| 2 | First oligonucleotide, target polynucleotide, RNase H |
| 3 | First oligonucleotide, second oligonucleotide, RNase H |
| 4 | First oligonucleotide, RNase H |

Figure 3:
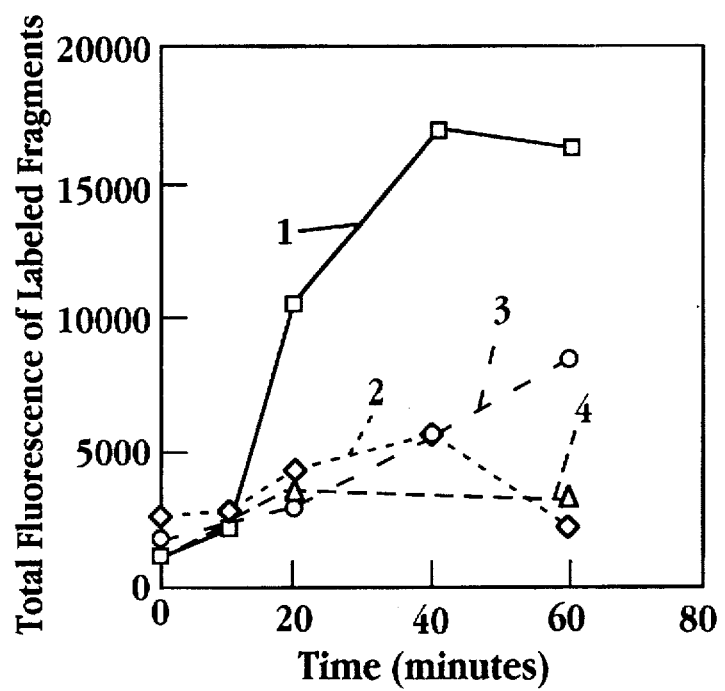
FIG. 3 illustrates data showing the amplification of DNA fragments in accordance with the invention.

The experiments were performed at 45° C. in 40 mM Tris-HCl (pH 7.6), 5 mM MgCl$_2$, 1 μL of beads, 1 μL target polynucleotide ($4.7 \times 10^{-8}$ pmol) were called for, 20 units of RNase Block (Stratagene, La Jolla, Calif.), and 0.8 units RNase H (Boehringer Mannheim, Indianapolis, Ind.). In experiments 1 and 3, 1 µL of beads contained 0.5 µL of the first oligonucleotide and 0.5 µL of the second oligonucleotide. In experiments 3 and 4, 1 µL of 40 mM Tris-HCl buffer solution was added in place of the target polynucleotide. For experiments 1 and 2, samples of the reaction mixture were taken at 0, 10, 20, 40, and 60 minutes and stopped by adding 5 µL of 100 mM EDTA. For experiments 3 and 4, samples of the reaction mixture were taken at 0, 20, and 60 minutes and stopped by adding 5 µL of 100 mM EDTA. After stopping the reactions, the samples were diluted with 40 mM Tris-HCl buffer (pH 7.6) to 120 µL, after which 3 µL aliquots were mixed with 12 µL of a loading dye (methylene blue) and analyzed on a Perkin-Elmer, Applied Biosystems Division model 373 DNA sequencer using a 6% polyacrylamide gel. The results are shown in FIG. 3, where individual data points at the various times indicate total fluorescence of the bands containing the separated first and second fragments. Curve 1 illustrates the data from experiment 1, curve 2 the data from experiment 2, curve 3 the data from experiment 3, and curve 4 the data from experiment 4.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

I claim:

1. A method of detecting a target polynucleotide, the method comprising the steps of:
 (a) providing a first oligonucleotide having
  (i) a nucleotide sequence complementary to a portion of a target polynucleotide and
  (ii) a scissile linkage within said portion which is cleavable by a selected cleaving agent whenever the first oligonucleotide forms a perfectly matched duplex with said portion such that a first fragment is released from the first oligonucleotide, the first fragment having a nucleotide sequence complementary to said portion of the target polynucleotide;
 (b) providing a second oligonucleotide having
  (i) a nucleotide sequence identical to that of said portion of the target polynucleotide and
  (ii) a scissile linkage within said portion which is cleavable by a selected cleaving agent which may be the same as or different from said first cleaving agent whenever the second oligonucleotide forms a perfectly matched duplex with the first fragment such that a second fragment is released from the second oligonucleotide, the second fragment having a nucleotide sequence complementary to said portion of the first oligonucleotide;

(c) maintaining the first oligonucleotide and the second oligonucleotide in substantial physical separation such that the formation of perfectly matched duplexes between any first oligonucleotides and any second oligonucleotides is inhibited and such that released first fragments may diffusibly communicate with the second oligonucleotides and released second fragments may diffusibly communicate with the first oligonucleotides; and (d) exposing the first and second oligonucleotides to the target polynucleotide in the presence of said cleaving agent(s) under conditions effective to cleave said scissile linkages when said duplexes are formed, and
  (i) wherein duplexes between the first oligonucleotide and the portion of the target polynucleotide, duplexes between the first oligonucleotide and the second fragment, and duplexes between the second oligonucleotide and the first fragment are stable, and
  (ii) wherein duplexes between cleaved first oligonucleotides and the second fragments and duplexes between cleaved second oligonucleotides and the first fragments are unstable, such that an increase in the concentrations of the first and second fragments is an indication of the presence of the target polynucleotide.

2. The method of claim 1 wherein said first oligonucleotides are attached to microparticles separate from said second oligonucleotides and wherein said second oligonucleotides are attached to microparticles separate from said first oligonucleotides.

3. The method of claim 2 wherein said scissile linkage of said first oligonucleotides comprises one or more segments of RNA and wherein said scissile linkage is cleaved by an RNase H activity of an enzyme.

4. The method of claim 3 wherein said scissile linkage of said second oligonucleotides comprises one or more segments of RNA and wherein said scissile linkage is cleaved by an RNase H activity of an enzyme.

5. The method of claim 4 wherein said first and said second oligonucleotides each have a single RNA segment between two and ten RNA monomers in length.

6. The method of claim 5 wherein said conditions for exposing said target polynucleotide to said first and second oligonucleotides are isothermal at a temperature in the range of 32° C. to 60° C.

7. The method of claim 2 wherein said scissile linkage of said first oligonucleotides comprises one or more restriction endonuclease cleavage sites each having a nuclease-resistant moiety on a single strand of said sites and wherein said scissile linkage is cleaved by a restriction endonuclease recognizing said site.

8. The method of claim 7 wherein said scissile linkage of said second oligonucleotides comprises one or more restriction endonuclease cleavage sites each having a nuclease-resistant moiety on a single strand of said sites and wherein said scissile linkage is cleaved by a restriction endonuclease recognizing said site.

9. The method of claim 8 wherein said first and said second oligonucleotides each have a single restriction endonuclease cleavage site.

10. The method of claim 9 wherein said conditions for exposing said target polynucleotide to said first and second oligonucleotides are isothermal at a temperature in the range of 32° C. to 60° C.

* * * * *